United States Patent
Knitowski et al.

(10) Patent No.: US 6,248,339 B1
(45) Date of Patent: Jun. 19, 2001

(54) FRAGRANT BODY LOTION AND CREAM

(75) Inventors: Mark Knitowski, Neshanic; Jeff Davis, Belle Meade, both of NJ (US)

(73) Assignee: Intimate Beauty Corporation, New York, NY (US)

( * ) Notice: Subject to any disclaimer, the term of this patent is extended or adjusted under 35 U.S.C. 154(b) by 0 days.

(21) Appl. No.: 09/374,901

(22) Filed: Aug. 13, 1999

(51) Int. Cl.⁷ .................. A61K 7/00; A61K 7/46
(52) U.S. Cl. .................. 424/401; 512/1; 514/944
(58) Field of Search .................. 424/401; 512/1; 514/944

(56) References Cited

U.S. PATENT DOCUMENTS

| | | | |
|---|---|---|---|
| 5,252,761 | * 10/1993 | Hirose et al. | 554/77 |
| 5,266,321 | * 11/1993 | Shukuzaki et al. | 424/401 |
| 5,486,566 | * 1/1996 | Katsoulis | 524/773 |
| 5,623,017 | * 4/1997 | Hill | 524/860 |
| 5,654,362 | * 8/1997 | Schulz, Jr. et al. | 524/862 |
| 5,846,550 | * 12/1998 | Perrin et al. | 424/401 |
| 5,891,470 | * 4/1999 | Rinaldi et al. | 424/451 |
| 5,919,437 | * 7/1999 | Lee et al. | 424/68 |
| 5,929,163 | * 7/1999 | Harashima | 524/837 |
| 5,942,215 | * 8/1999 | Edwards et al. | 424/65 |
| 5,972,320 | * 10/1999 | Moloney et al. | 424/65 |
| 5,977,280 | * 11/1999 | Kadlec et al. | 528/15 |
| 5,980,921 | * 11/1999 | Biedermann et al. | 424/401 |
| 6,027,738 | * 2/2000 | Stepniewski et al. | 424/401 |
| 6,083,900 | * 7/2000 | Auguste et al. | 512/2 |

FOREIGN PATENT DOCUMENTS

405074261 * 3/1993 (JP).

* cited by examiner

*Primary Examiner*—Shelley A. Dodson
*Assistant Examiner*—Marina Lamm
(74) *Attorney, Agent, or Firm*—Colluci & Umans; Peter C. Michalos; Angelo Notaro

(57) ABSTRACT

A water-free and alcohol-free skin care and fragrance composition contains about 60 to 90 percent by weight cyclomethicone/dimethicone crosspolymer gel and about 1 to 20 percent by weight fragrance. A method of applying fragrance to skin comprises applying to the skin this composition.

5 Claims, No Drawings

FRAGRANT BODY LOTION AND CREAM

FIELD AND BACKGROUND OF THE INVENTION

The present invention relates in general to creams and lotions, and in particular to a new and useful fragrant body lotion or cream which improves fragrance lift in a non-alcohol carrier and creates a barrier to let the fragrance adhere to the skin to lengthen the duration of fragrance emission, while maintaining skin moisture.

U.S. Pat. No. 5,623,017 to Hill, assigned to Dow Corning Corporation, discloses a clear silicone gel which is used to improve the characteristics of various cosmetic products. One such cosmetic product is disclosed in U.S. Pat. No. 5,919,437 to Lee, et al., assigned to Colgate-Palmolive Company, which utilizes a combination of the silicone gel material with an active ingredient such as deodorant, antiperspirant, sunscreen, insect repellant or anti-fungal agent. Also see U.S. Pat. No. 4,673,570 to Soldati, assigned to Carter-Wallace, Inc., for an antiperspirant gel composition.

The Hill patent also identifies a class of cyclic volatile methyl siloxanes by the International Nomenclature Cosmetic Ingredient (INCI) name "CYCLOMETHICONE."

U.S. Pat. No. 5,654,362 to Schulz, Jr., et al., assigned to Dow-Corning Corporation, discloses a silicone oil and solvent composition for use in cosmetics.

U.S. Pat. Nos. 5,623,017 and 5,654,362 are incorporated here by reference for their teaching of cyclomethicone/dimethicone crosspolymer gels.

SUMMARY OF THE INVENTION

The present invention is a unique composition and method of using that composition which has an improved feel on the skin, improves fragrance lift from the skin and, at the same time, moisturizes the skin and acts as a barrier to help maintain moisture and repair the skin.

The composition of the invention, which is a lotion or cream, advantageously uses a cyclomethicone/dimethicone crosspolymer such as that disclosed in U.S. Pat. No. 5,654, 362 to Schulz, Jr., et al. and contains no alcohol. The inventors have found that by using this silicone gel, shortly after the composition is spread onto the skin, some of the cyclomethicone portion flash evaporates to provide a rapid initial release of fragrance into the air. Additional fragrance, however, is held against the skin by the dimethicone crosspolymer and, at the same time, improves the smooth feel on the skin and moisturizing of the skin. The remaining fragrance is slowly released, due to the remaining dimethicone crosspolymer, in an advantageous and unexpected manner.

The cyclomethicone/dimethicone crosspolymer is also used in selected proportions, to adjust the viscosity of the composition to make it either a lotion (low viscosity) or a cream (high viscosity).

Accordingly, an object of the present invention is to provide a skin care and fragrance applying composition comprising about 60–90% by weight cyclomethicone/dimethicone crosspolymer gel and about 1–20% by weight fragrance.

A further object of the present invention is to provide a method of moisturizing and adding fragrance to the skin comprising applying the composition to the skin.

A still further object of the present invention is to provide a composition and method of using the composition which is free of water and free of alcohol, and which adds a smooth, pleasing feel to the skin while metering release of fragrance from the skin and maintaining moisture level in the skin.

The various features of novelty which characterize the invention are pointed out with particularity in the claims annexed to and forming a part of this disclosure. For a better understanding of the invention, its operating advantages and specific objects attained by its uses, reference is made to the accompanying descriptive matter in which preferred embodiments of the invention are illustrated.

DESCRIPTION OF THE PREFERRED EMBODIMENTS

The body lotion or cream of the invention contains about 60 to 90 wght. % anhydrous cyclomethicone/dimethicone crosspolymer with about 1 to 20 wght. % fragrance oil (e.g., Firmenich Sexy Angel-121.623/B). The formula contains no water or alcohol. The viscosity of the system is dependent on the level of cyclomethicone/dimethicone crosspolymer in which the level of the cyclomethicone is 65.2% of the blend and the dimethicone crosspolymer is 8.8% of the blend which accounts for 74.0% of the formula in the preferred embodiment of the lotion. The higher viscosity cream has a preferred 79.6% content in the composition.

The preferred lotion system also contains hydrocarbons linked to a copolymer. Isohexadecane (hydrocarbon) at 7.6% to 8/0% of the blend with hydrogenated butylene ethylene styrene copolymer and hydrogenated butylene ethylene propylene styrene copolymer between 0.1% and 1.0% makes up 8% of the formula. The formula contains an ester of isononyl isonanoate at 14.79%. The product utilizes titanium dioxide, zinc oxide and mica to achieve opacity in the product at a level of 0.1% to 1.0%. All amounts are in percent by weight.

The lotion product uses the cyclomethicone/dimethicone crosspolymer to provide a fragrance lift that is usually found in alcohol type products. The product facilitates barrier repair and moisturizes the skin for up to eight hours (all day). The product is a free flowing lotion. A decrease in the amount of cyclomethicone/dimethicone crosspolymer not only decreases the viscosity, but also has a dramatic affect on the feel of the product. The viscosity range for the lotion is about 30,000 to 40,000 cps. The product loses the slip and becomes more tacky by lowering the level below about 60% cyclomethicone/dimethicone crosspolymer.

A benefit of the lotion system is that it provides maximum fragrance lift in a non-alcohol carrier and creates a barrier to let the fragrance adhere to the skin hence lengthening the duration of the fragrance. Unlike alcohol products, which are drying, this inventive formula provides moisture to the skin but allows for great fragrance integrity. The product has such a unique feel it can not be compared to any other fragrance body product on the market. The product has a silky feel to the touch and leaves skin soft and smooth without any residual on, or tack to the skin. It moisturizes the skin and facilitates barrier repair to keep skin healthy longer.

The lotion and cream products may use any compatible fragrance oil, any hydrocarbons linked to a copolymer and any opacifing agent or chemical which would give the product an opaque appearance, all of which, however, must be acceptable for topical use.

The cream of the present invention has an anhydrous cyclomethicone/dimethicone crosspolymer with fragrance oil (e.g., Firmenich Sexy Angel-143.131/B or 121.623/B) at between about 1% to 20%. The formula again contains no water or alcohol. The viscosity of the system, is dependent on the level of cyclomethicone/dimethicone crosspolymer, has a level of the cyclomethicone at 69.25% of the blend and the dimethicone crosspolymer at least 10.35% of the blend which together accounts for 79.6% of the formula in the preferred cream. The formula contains the hydrocarbon isododecane at a 11.05% level. The formula contains an ester of isononyl isonanoate at 5.95%. The product utilizes titanium dioxide, zinc oxide pearl and mica to achieve opacity in the product at a level of 0.1% to 1.0%.

As with the lotion, the cream product uses the cyclomethicone/dimethicone crosspolymer to provide a fragrance lift that is usually found in alcohol type products. The product works to facilitate barrier repair and moisturizes the skin for up to eight hours. The cream is more viscus than the lotion. A decrease in the amount of cyclomethicone/ dimethicone crosspolymer would not only decreases the viscosity, but also has a dramatic affect on the feel of the product. If the dimethicone crosspolymer content is below 10% the product will not form a cream. The viscosity range for the cream is about 125,000 to 135,000 cps. The product loses the slip and becomes more tacky by lowering the level to below about 60% cyclomethicone/dimethicone crosspolymer.

The benefit of the cream system is that is provides maximum fragrance lift in a non-alcohol carrier, creates a barrier to let the fragrance adhere to the skin hence lengthening the duration of the fragrance. Unlike alcohol products, which are drying, this formula provides moisture to the skin but allows for great fragrance integrity. As with the lotion, the cream product has such a unique feel that it can not be compared to any other fragrance body product on the market. The product has a silk feel to the touch; leaves skin soft and smooth without any residue or tack to the skin. It works to moisturize the skin and to facilitate barrier repair to keep skin healthy longer.

As with the lotion, the cream could use any fragrance oil, any hydrocarbons linked to a copolymer and any opacifing agent or chemical which would give the product an opaque appearance and which are skin compatible.

The following tables list the ingredients and composition of the preferred lotion and cream of the present invention, as well as advantageous ranges for the various ingredients. Throughout this disclosure, where the term "composition" is used, it is meant to include either a lotion or a cream, formulated according to the present invention and having the advantages of the present invention.

TABLE 1

LOTION

| INGREDIENTS | PREFERRED WEIGHT % | RANGE IN WEIGHT % |
|---|---|---|
| DC9040* (silicone gel) | 74.00 | 60–90 |
| DERMOL 99 (isononyl isonanoate) | 14.79 | 4–20 |
| VERSAGEL M3750** (isohexadecane 95–99%) | 8.00 | 4–11 |
| FRAG.121.623/B (fragrance oil) | 2.50 | 1–20 |
| MICRONA MATTE WHITE (opacifing agent/titanium dioxide/mica/zinc oxide) | 0.34 | 0.1–1.0 |
| LIQUPAR OIL (isopropylparaben/isobutyl- paraben/butylparaben) | 0.20 | 0.1–0.5 |

TABLE 1-continued

LOTION

| INGREDIENTS | PREFERRED WEIGHT % | RANGE IN WEIGHT % |
|---|---|---|
| SPHERON L1500 (silica) | 0.17 | 0.05–0.3 |

*cyclomethicone 88 wght %/dimethicone crosspolymer 12 wght %.
**plus 1–5% hydrogenated butylene ethylene styrene copolymer and ethylene propylene styrene copolymer.
***dimethicone crosspolymer should be present in an amount of about 5–12 wght % for the lotion or the cream.

TABLE 2

CREAM

| INGREDIENTS | PREFERRED WEIGHT % | RANGE IN WEIGHT % |
|---|---|---|
| DC9040* (silicone gel) | 79.60 | 60–90 |
| DERMOL 99 (isononyl isonanoate) | 5.95 | 1–11 |
| PERMETHYL 99A (isododecane) | 11.05 | 5–17 |
| FRAG.143.131/B (fragrance oil) | 2.50 | 1–20 |
| MICRO MATTE WHITE (zinc oxide, opacifing agent w/titanium dioxide and mica), | 0.7 | 1–5 |
| LIQUPAR OIL (isopropylparaben/isobutyl- paraben/butylparaben) | 0.20 | 0.1–0.5 |

*cyclomethicone 87 wght %/dimethicone crosspolymer 13 wght %.

Clinical Testing

Subjects: Eight female subjects ages 35–55 with dry skin, especially on the lower legs were used in this study to evaluate the ability of various test materials to facilitate the repair of a damaged skin water barrier.

Test Site: The outer aspect of the lower legs which normally has dry skin was used as the test site for this study. A required condition of the test was that subjects had visibly dry skin and a TEWL (a measure of skin dryness) of at least 3.5–4 mg/cm2/hr on the lower legs prior to skin conditioning.

TEWL or Transepidermal Water Loss, measures skin barrier function. An electrical measurement of conductance of water in the skin is taken. The lower the number, the less water loss occurs through the skin barrier and the more "repair" and maintenance of the skin barrier occurs.

For 2 days prior to the study, subjects washed their lower legs three times a day with 5% sodium lauryl sulfate (SLS) to induce further increases in TEWL. Subjects visited the test center daily and TEWL were monitored. Subjects were considered acceptable for the study when their TEWL had reached a value of at least 8 mg/cm2/hr with no signs of irritation clinically, or as evidenced by increased blood flow on the treated area. It was found that normal skin has a TEWL of between 2–3 mg/cm2/hr. Eight test sites were defined, four on each leg with a template, each site being at least 3×3 cm. The sites were on the mid-line of the outer lower leg. The upper site was approximately 2–6 cm blow the knee and about 2–6 cm apart.

Pre-Conditioning of Subjects: Subjects were instructed not to use moisturizer on their lower leg during the conditioning and test-phase of the study. They were instructed on how to apply the test materials.

Product Application: The compositions of the invention were applied twice a day, in the morning and evening, after bathing, on the defined areas at an instructed dose of about 3 mg/cm2. An individualized template was given to each subject to aid in product application. Test sites and individual products were color coded to avoid misapplication. If desired by a subject, the morning application was made at the test center daily. Note the barrier disruptive treatments were not continued during the treatment phase.

Evaluations: TEWL was measured on each test site after 1 hour equilibration at 70° C. and 40% RH with subject restrictions as in the previous TEWL study. On the day of test measurements, no product was applied that morning. Measurements were made in triplicate and averaged. If any of the readings varied by more than 25% from the mean of the other readings, the subjects were re-equilibrated and re-tested. Measurements were made on day 1 prior to test product application. The same measurements were made on day 7 and on day 14 also, if the subject wished.

Test Materials: The following test materials (including controls) were used in this study: inventive cream, inventive lotion, 1% ceramide mix, petrolatum 100%, inventive cream supplemented with 0.5% ceramide mix.

Results: The results are described in the following table. As can be seen, the study was run for seven days. At the end of the study, the untreated controls (no treatment and carbopol) had not yet returned back to pre-SLS baseline values (about 3), however, this would be expected to occur within several days. The two positive controls, petrolatum (100%) and a ceramide mix (1%) were very effective at facilitating barrier repair. TEWL rates returned back to normal within 4–5 days. The petrolatum was more effective early on, but the ceramide started to work better after 3–4 days. The cream and lotion of the invention, both, facilitated barrier repair (about 33% and 44% respectively at day 4) with the lotion somewhat barrier. As a control when ceramide was added to the cream, barrier repair characteristics improved considerably (75% at day 4). The results herein suggest that both Gryphon prototypes with facilitate barrier repair, on subjects with damaged barriers, such as older individuals and subjects with very dry skin.

TABLE 3

CLINICAL TESTING/RESULTS

| COMPOSITION | BL | Day 1 | Day 3 | Day 4 | Day 5 | Day 7 |
|---|---|---|---|---|---|---|
| No Treatment | 8.94 | 8.33 | 6.6 | 6.5 | 6.3 | 4.45 |
| Carbopol Gel | 8.45 | 7.77 | 7.04 | 5.78 | 5.02 | 4.56 |
| Petrolatum | 9.03 | 5.64 | 4.03 | 3.44 | 3.25 | 3.27 |
| 1% Ceramide | 8.82 | 6.88 | 5.12 | 3.83 | 3.05 | 3.12 |
| Cream | 9.13 | 7.67 | 6.04 | 5.34 | 4.04 | 3.24 |
| Lotion | 9.16 | 7.04 | 5.78 | 4.96 | 3.89 | 3.20 |
| Cream & Ceramide | 9.06 | 6.89 | 5.26 | 3.89 | 3.45 | 3.12 |

The essential ingredient of the present invention is the gel. Cyclomethicone/dimethicone crosspolymer gel is by far the preferred gel, but an equivalent gel having the same or similar characteristics can also be used in the composition.

While a specific embodiment of the invention has been shown and described in detail to illustrate the application of the principles of the invention, it will be understood that the invention may be embodied otherwise without departing from such principles.

What is claimed is:

1. A skin care and fragrancing composition without water and without alcohol, the composition being a lotion or cream, and consisting essentially of:

about 60–90% wt. cyclomethicone/dimethicone crosspolymer gel which is formed using organic cross-linking agents only;

about 1–20% wt. fragrance;

about 0.5–10% wt. opacifying agent;

about 4–20% wt. isononyl isononanoate; and about 5–15% wt. of at least one hydrocarbon which includes at least one of isohexadecane and isododecane, and, if isohexadecane is present, at least one hydrogenated styrene copolymer.

2. A composition according to claim 1, wherein the amount of gel is selected to give the composition a viscosity of about 30,000–40,000 cps, so that the composition is a lotion, the hydrocarbon being isohexadecane and the hydrogenated styrene copolymer includes both hydrogenated butylene ethylene styrene and hydrogenated ethylene styrene propylene styrene copolymers.

3. A composition according to claim 1, wherein the amount of gel is selected to give the composition a viscosity of about 125,000–135,000 cps, so that the composition is a cream, the hydrocarbon being isododecane.

4. A composition according to claim 1, wherein the opacifying agent is selected from the group consisting of silica, titanium dioxide, zinc oxide, mica and mixtures thereof.

5. A method for moisturizing and applying a fragrance to skin, comprising applying to the skin a composition which is without water and without alcohol, the composition being a lotion or cream, and consisting essentially of:

about 60–90% wt. cyclomethicone/dimethicone crosspolymer gel which is formed using organic cross-linking agents only;

about 1–20% wt. fragrance;

about 0.5–10% wt. opacifying agent;

about 4–20% wt. isononyl isononanoate; and about 5–15% wt. of at least one hydrocarbon which includes at least one of isohexadecane and isododecane, and, if isohexadecane is present, at least one hydrogenated styrene copolymer.

\* \* \* \* \*